US00PP13596P3

(12) United States Plant Patent
Trees

(10) Patent No.: US PP13,596 P3
(45) Date of Patent: Feb. 25, 2003

(54) ANTHIRRHINUM PLANT NAMED 'BALUMPINK'

(75) Inventor: Scott Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/808,532

(22) Filed: Mar. 14, 2001

(65) Prior Publication Data

US 2001/0047529 P1 Nov. 29, 2001

(51) Int. Cl.[7] ..... A01H 5/00
(52) U.S. Cl. ..... Plt./322

(58) Field of Search ..... Plt./322

(56) References Cited

PUBLICATIONS

UPOV–ROM GTITM Computer Database, 2001/06, GTI Jouve Retrieval Software, citation for 'Balumpink'.*

* cited by examiner

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Antirrhinum plant named 'Balumpink' characterized by its trailing habit, dark green glabrous foliage and pink flowers.

2 Drawing Sheets

LATIN NAME OF THE GENUS AND SPECIES OF PLANT CLAIMED

*Antirrhinum majus.*

VARIETY DENOMINATION

'Balumpink'.

BACKGROUND OF THE INVENTION

The present invention comprises a new and distinct Antirrhinum plant, hereinafter referred to by the cultivar name 'Balumpink'. This new cultivar was developed by the inventor through a controlled breeding program during August 1997 at Arroyo Grande, Calif. The objective of the breeding program was the development of Antirrhinum cultivars with trailing mounded habit, continuous flowering, excellent basal branching and small, dark green foliage.

'Balumpink' resulted from the self fertilization of the proprietary antirrhinum plant designated 90-2 which is characterized by its compact habit, purple flowers and medium green glabrous foliage. The resulting seed was collected and germinated. From the flowering progeny, a plant was selected in April 1998 and initially designated 229-2.

Asexual reproduction of the new cultivar by terminal or stem cuttings taken during 1998 and 1999 at Arroyo Grande, Calif., U.S.A. has demonstrated that the characteristics of the new cultivar as herein described are firmly fixed and retained through successive generations of such asexual propagation.

SUMMARY OF THE INVENTION

It was found that the cultivar of the present invention:

(a) Exhibits a trailing habit, (b) Forms abundant bright pink flowers, and (c) Exhibits dark green foliage.

When the new cultivar of the present invention is compared to Candelabra 'Rose Pink' (not patented in the United States) it is found that the new cultivar exhibits a somewhat less trailing habit, larger foliage with a different texture and flowers that differ in color and fragrance as detailed in TABLE 1, below.

TABLE 1

| CHARACTERISTIC | 'BALUMPINK' | CANDELABRA 'ROSE PINK' |
|---|---|---|
| PLANT WIDTH - cm | 28 cm | 31.8 cm |
| MATURE LEAF LENGTH × WIDTH - cm | 3.3 × 1.8 | 1.2 × 1 |
| LEAF SHAPE | OVATE | OVAL |
| LEAF TEXTURE | GLABROUS | PUBESCENT |
| FLOWER COLOR | 62A | 72B |
| FLOWER FRAGRANCE | NONE | SWEET |
| FLOWER LENGTH × WIDTH OF LOWER LIP - cm | 3.4 × 1.7 | 3.3 × 1.6 |

BRIEF DESCRIPTION OF PHOTOGRAPHS

The accompanying photographs show as nearly true as it is reasonably possible to make the same in color illustrations of this type, typical flower and foliage characteristics of the new cultivar.

Figure 1:
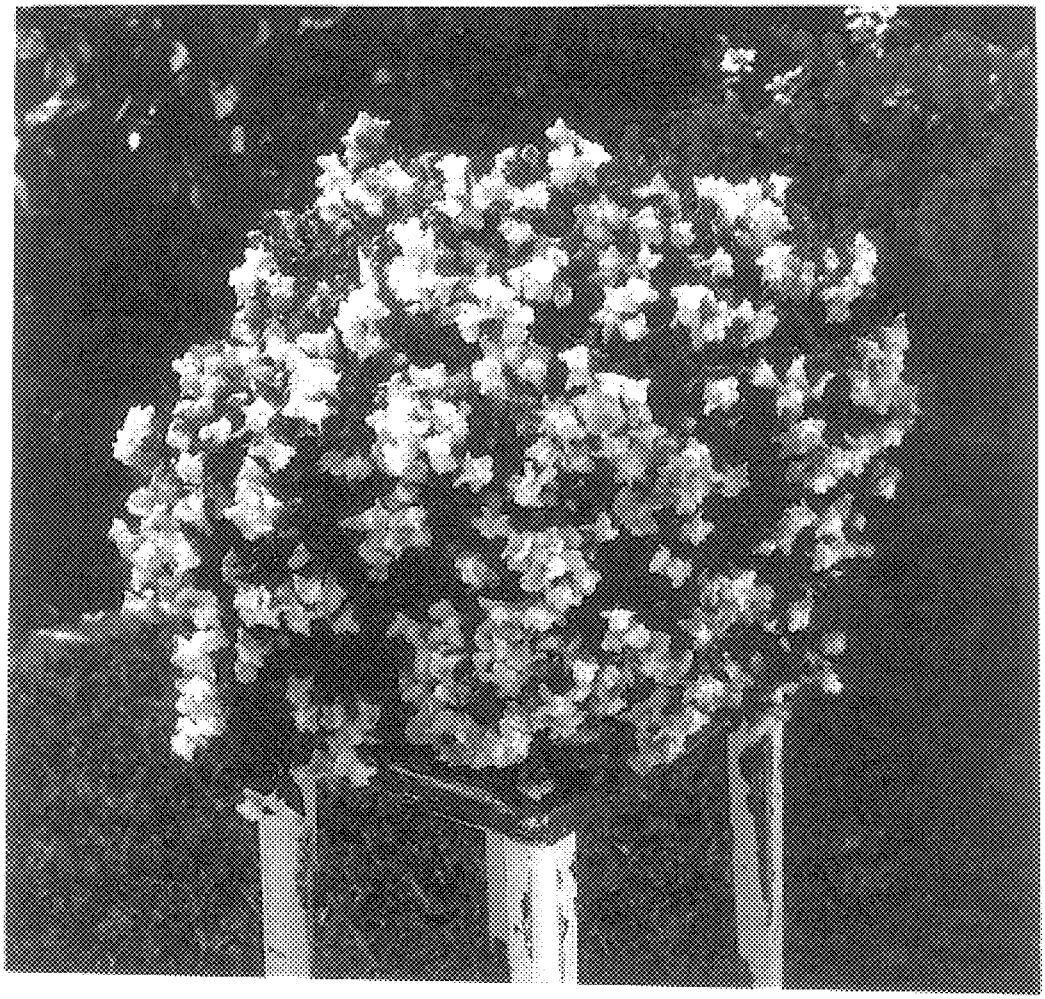

FIG. 1 comprises a view of the growth habit of 'Balumpink' in a pot containing four plants.

Figure 2:
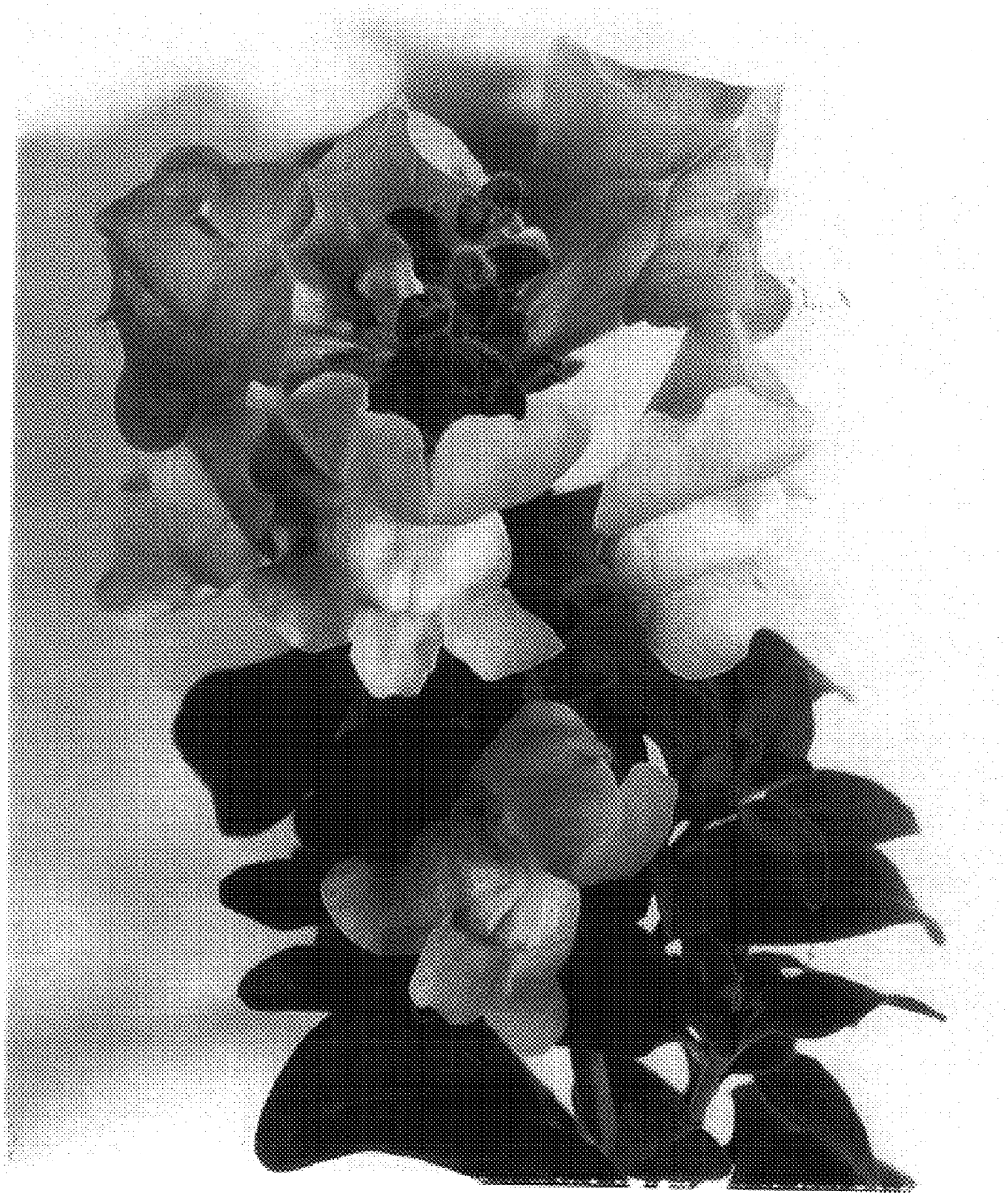

FIG. 2 comprises a close-up view of typical flowers and foliage of 'Balumpink'.

Colors are darker than the actual flower and foliage colors.

The plants were grown in a greenhouse at West Chicago, Ill., USA.

DETAILED BOTANICAL DESCRIPTION

The Balumpink cultivar has not been observed under all possible environmental conditions to date. Accordingly, it is possible that the phenotype may vary somewhat with variations in the environment, such as temperature, light intensity and day length.

The chart used in the identification of colors described herein is The R.H.S Colour Chart of The Royal Horticultural Society, London, England. The color values were determined on Sep. 26, 2000 in West Chicago, Ill. The readings were taken between 11:00 and 11:45 p.m. under natural light conditions. The plants were produced from cuttings taken from stock plants and grown for ten (10) weeks in a double polycarbonate covered greenhouse under conditions comparable to those used in commercial practice while utilizing a soilless growth medium and maintaining temperatures of approximately 72° F. during the day and approximately 65° F. during the night.

Classification:

*Botanical.*—*Antirrhinum majus* cultivar 'Balumpink'.

*Commercial.*—Trailing Snapdragon.

Propagation:

*Type cutting.*—Terminal tip.

*Time to initate roots.*—Approximately 10–14 days with the shorter times generally being experienced in the summer and the longer times in the winter.

*Root description.*—Fibrous, branching.

Plant description:

*General appearance and form.*—Mounded and trailing.

*Plant length (from top of plant plane to lower flowers).*—Approximately 16 cm.

*Foliage width.*—Approximately 28 cm.

*Branching habit.*—Freely branching. Pinching encourages branching.

*Stem.*—Diameter at lowest node approximately 5 mm, closest to 146B in color, smooth in texture.

*Internode length.*—Approximately 2.2 cm.

Foliage description:

*Shape.*—Ovate, acute apex, attenuate base, entire margin.

*Arrangement.*—Opposite.

*Venation pattern.*—Arcuate.

*Texture.*—Upper and lower surface: smooth.

*Color of mature foliage.*—Upper surface closest to 137A with venation of 146A, lower surface closest to 146A with venation of 146A.

*Size of mature leaves.*—Approximately 3.3 cm in length, approximately 1.8 cm in width.

*Petiole.*—Length is approximately 3 mm, diameter is approximately 1 mm, color is 146A, texture is smooth.

Flower description:

*Flowering habit.*—'Balumpink' is freely flowering under outdoor growing conditions with substantially continuous blooming from spring until fall.

*Flower arrangement.*—Terminal racemes.

*Peduncle.*—Length is approximately 9 mm, diameter is approximately 1 mm, color is closest to 146D.

*Flower.*—Approximately 3.2 cm in length, bilabiate. Lip texture is smooth, margin entire and somewhat undulating. Upper lip is 2 parted, approximately 1.8 cm long, approximately 2.3 cm wide, 62A at margins fading to 62D where lip meets palate. Lower lip is 3 parted, approximately 1.3 cm in length, approximately 2 cm in width, 62A at edges fading to 62D with two areas of 6A where lip meets palate. The palate is 155D and covered with hairs of 155D. Inside throat is 155D with hairs of 6A and venation of 63C, outside throat is between 62C and 62D.

*Flower fragrance.*—None.

*Flower bud.*—Length is approximately 1.9 cm, width is approximately 9 mm, texture is pilose.

*Calyx.*—5 sepals, approximately 8 mm in length, approximately 4 mm in width, ovate with acute apex, surface is pilose, upper and lower surface color is closest to 137C.

*Reproductive organs.*—Androecium: 4 stamens, 2 are 1.8 cm in length; 155D; 2 are 1.4 cm in length 155D with slight anthocyanin coloration. Anthers approximately 2 mm in length, color is 12D. Pollen color is closest to 12A. Gynoecium: one pistil. Stigma length is approximately 2 mm, color is 144B. Style is approximately 1.4 cm in length, color is 144D with slight anthocyanin coloration. Ovary is 2 mm in diameter and hoary.

Seed production: Seed production has not been observed.

Disease resistance: Resistance to pathogens is not claimed.

Hardiness: Plants of the new cultivar are hardy in zones 9 and above.

Drought/heat tolerance: Plants of the new cultivar have not been observed to exhibit any exceptional tolerance to drought or heat.

I claim:

1. A new and distinct cultivar of Antirrhinum plant named 'Balumpink' substantially as herein shown and described, which:

(a) Exhibits a trailing a trailing growth habit, (b) Forms abundant bright pink flowers, and (c) Exhibits dark green foliage.

* * * * *